(12) United States Patent
Rubinsky et al.

(10) Patent No.: US 8,114,070 B2
(45) Date of Patent: Feb. 14, 2012

(54) METHODS AND SYSTEMS FOR TREATING BPH USING ELECTROPORATION

(75) Inventors: Boris Rubinsky, Albany, CA (US); Gary Onik, Orlando, FL (US); Paul Mikus, Coto de Caza, CA (US)

(73) Assignee: AngioDynamics, Inc., Latham, NY (US)

( * ) Notice: Subject to any disclaimer, the term of this patent is extended or adjusted under 35 U.S.C. 154(b) by 1649 days.

(21) Appl. No.: 11/166,974

(22) Filed: Jun. 24, 2005

(65) Prior Publication Data

US 2006/0293713 A1    Dec. 28, 2006

(51) Int. Cl.
*A61B 18/18* (2006.01)
(52) U.S. Cl. ............ 606/32; 607/115; 607/2; 435/173.6
(58) Field of Classification Search .............. 606/27–31, 606/42; 607/2, 3, 72, 101, 102, 115, 116; 604/20–22; 435/173.6, 285.2
See application file for complete search history.

(56) References Cited

U.S. PATENT DOCUMENTS

| | | |
|---|---|---|
| 1,653,819 A | 12/1927 | Northcott et al. |
| 4,016,886 A | 4/1977 | Doss |
| 4,226,246 A | 10/1980 | Fragnet |
| 4,262,672 A | 4/1981 | Kief |
| 4,407,943 A | 10/1983 | Cole et al. |
| 4,810,963 A | 3/1989 | Blake-Coleman et al. |
| 4,907,601 A | 3/1990 | Frick |
| 4,946,793 A | 8/1990 | Marshall, III |
| 5,019,034 A | 5/1991 | Weaver et al. ............ 604/20 |
| 5,052,391 A | 10/1991 | Silberstone et al. |
| 5,058,605 A | 10/1991 | Slovak |
| 5,098,843 A | 3/1992 | Calvin |
| 5,134,070 A | 7/1992 | Casnig |
| 5,173,158 A | 12/1992 | Schmukler |
| 5,193,537 A | 3/1993 | Freeman |
| 5,273,525 A | 12/1993 | Hofmann |
| 5,283,194 A | 2/1994 | Schmukler |
| 5,318,563 A | 6/1994 | Malis et al. |
| 5,328,451 A | 7/1994 | Davis et al. |
| 5,389,069 A | 2/1995 | Weaver |

(Continued)

FOREIGN PATENT DOCUMENTS

DE                863111            1/1953

(Continued)

OTHER PUBLICATIONS

J.C. Weaver, et al., "Theory of Electroporation; A Review" Bioelectrochemistry and Bioenergetics, vol. 41, pp. 135-160, 1996.

(Continued)

*Primary Examiner* — Michael Peffley
(74) *Attorney, Agent, or Firm* — Harry K. Ahn; Abelman Frayne & Schwab (57) ABSTRACT

A system for treating benign prostate hyperplasia (BPH) of a prostate. At least first and second mono-polar electrodes are configured to be introduced at or near a BPH tissue site of the prostate gland of the patient. A voltage pulse generator is coupled to the first and second mono-polar electrodes. The voltage pulse generator is configured to apply sufficient electrical pulses between the first and second mono-polar electrodes to induce electroporation of cells in the BPH tissue site, to create necrosis of cells of the BPH tissue site, but insufficient to create a thermal damaging effect to a majority of the BPH tissue site.

84 Claims, 3 Drawing Sheets

U.S. PATENT DOCUMENTS

| | | | | |
|---|---|---|---|---|
| 5,403,311 | A | 4/1995 | Abele et al. | |
| 5,425,752 | A | 6/1995 | Vu'Nguyen | |
| 5,439,440 | A | 8/1995 | Hofmann | |
| 5,458,625 | A | 10/1995 | Kendall | |
| 5,533,999 | A | 7/1996 | Hood et al. | |
| 5,536,240 | A | 7/1996 | Edwards et al. | |
| 5,575,811 | A | 11/1996 | Reid et al. | |
| 5,626,146 | A | 5/1997 | Barber et al. | |
| 5,634,899 | A | 6/1997 | Shapland et al. | |
| 5,674,267 | A | 10/1997 | Mir et al. | |
| 5,702,359 | A | 12/1997 | Hofmann | |
| 5,720,921 | A | 2/1998 | Meserol | |
| 5,778,894 | A | 7/1998 | Dorogi et al. | |
| 5,782,882 | A | 7/1998 | Lerman et al. | |
| 5,800,378 | A | 9/1998 | Edwards et al. | |
| 5,810,762 | A | 9/1998 | Hofmann | |
| 5,836,905 | A | 11/1998 | Lemelson et al. | |
| 5,843,026 | A | 12/1998 | Edwards et al. | |
| 5,873,849 | A | 2/1999 | Bernard | |
| 5,919,142 | A | 7/1999 | Boone et al. | |
| 5,947,889 | A | 9/1999 | Hehrlein | |
| 5,983,131 | A | 11/1999 | Weaver et al. | |
| 5,991,697 | A | 11/1999 | Nelson et al. | |
| 5,999,847 | A | 12/1999 | Elstrom | |
| 6,009,347 | A | 12/1999 | Hofmann | |
| 6,010,613 | A | 1/2000 | Walters et al. | |
| 6,016,452 | A | 1/2000 | Kasevich | |
| 6,041,252 | A | 3/2000 | Walker et al. | |
| 6,055,453 | A | 4/2000 | Hofmann et al. | 604/21 |
| 6,068,650 | A | 5/2000 | Nanda et al. | |
| 6,085,115 | A | 7/2000 | Weaver et al. | |
| 6,090,106 | A | 7/2000 | Goble et al. | 606/41 |
| 6,102,885 | A | 8/2000 | Bass | |
| 6,106,521 | A | 8/2000 | Blewett et al. | |
| 6,109,270 | A | 8/2000 | Mah et al. | 128/920 |
| 6,122,599 | A | 9/2000 | Mehta | |
| 6,132,419 | A | 10/2000 | Hofmann | |
| 6,159,163 | A | 12/2000 | Strauss et al. | |
| 6,208,893 | B1 | 3/2001 | Hofmann | |
| 6,210,402 | B1 | 4/2001 | Olsen et al. | |
| 6,212,433 | B1 | 4/2001 | Behl | 607/101 |
| 6,216,034 | B1 | 4/2001 | Hofmann | |
| 6,219,577 | B1 | 4/2001 | Brown et al. | |
| 6,241,702 | B1 | 6/2001 | Lundquist et al. | |
| 6,261,831 | B1 | 7/2001 | Agee | |
| 6,278,895 | B1 | 8/2001 | Bernard | |
| 6,300,108 | B1* | 10/2001 | Rubinsky et al. | 435/173.6 |
| 6,326,177 | B1* | 12/2001 | Schoenbach et al. | 435/173.7 |
| 6,347,247 | B1 | 2/2002 | Dev et al. | |
| 6,349,233 | B1 | 2/2002 | Adams | |
| 6,351,674 | B2 | 2/2002 | Silverstone | |
| 6,387,671 | B1 | 5/2002 | Rubinsky et al. | 435/173.7 |
| 6,403,348 | B1 | 6/2002 | Rubinsky et al. | |
| 6,470,211 | B1 | 10/2002 | Ideker et al. | |
| 6,482,619 | B1 | 11/2002 | Rubinsky et al. | |
| 6,493,592 | B1 | 12/2002 | Leonard et al. | |
| 6,500,173 | B2 | 12/2002 | Underwood et al. | |
| 6,526,320 | B2 | 2/2003 | Mitchell | |
| 6,562,604 | B2 | 5/2003 | Rubinsky et al. | |
| 6,607,529 | B1 | 8/2003 | Jones et al. | |
| 6,611,706 | B2 | 8/2003 | Avrahami et al. | 604/20 |
| 6,613,211 | B1 | 9/2003 | McCormick et al. | |
| 6,627,421 | B1 | 9/2003 | Unger et al. | |
| 6,653,091 | B1 | 11/2003 | Dunn et al. | |
| 6,669,691 | B1 | 12/2003 | Taimisto | |
| 6,692,493 | B2 | 2/2004 | McGovern et al. | |
| 6,697,669 | B2 | 2/2004 | Dev et al. | |
| 6,697,670 | B2 | 2/2004 | Chornenky et al. | |
| 6,702,808 | B1 | 3/2004 | Kreindel | |
| 6,795,728 | B2 | 9/2004 | Chornenky et al. | |
| 6,801,804 | B2 | 10/2004 | Miller et al. | |
| 6,865,416 | B2 | 3/2005 | Dev et al. | |
| 6,892,099 | B2 | 5/2005 | Jaafar et al. | |
| 6,912,417 | B1 | 6/2005 | Bernard et al. | |
| 6,927,049 | B2 | 8/2005 | Rubinsky et al. | |
| 6,962,587 | B2* | 11/2005 | Johnson et al. | 606/41 |
| 6,972,014 | B2 | 12/2005 | Eum et al. | |
| 6,994,706 | B2* | 2/2006 | Chornenky et al. | 606/41 |
| 7,053,063 | B2 | 5/2006 | Rubinsky et al. | |
| 7,063,698 | B2 | 6/2006 | Whayne et al. | |
| 7,130,697 | B2* | 10/2006 | Chornenky et al. | 607/101 |
| 7,211,083 | B2 | 5/2007 | Chornenky et al. | |
| 7,267,676 | B2 | 9/2007 | Chornenky et al. | |
| 2001/0044596 | A1 | 11/2001 | Jaafar | |
| 2002/0010491 | A1 | 1/2002 | Schoenbach et al. | 607/2 |
| 2002/0055731 | A1 | 5/2002 | Atala et al. | |
| 2002/0077676 | A1 | 6/2002 | Schroeppel et al. | |
| 2002/0099323 | A1 | 7/2002 | Dev et al. | |
| 2002/0138117 | A1 | 9/2002 | Son | |
| 2002/0193831 | A1 | 12/2002 | Smith, III | |
| 2003/0009110 | A1 | 1/2003 | Tu et al. | 600/547 |
| 2003/0060856 | A1* | 3/2003 | Chornenky et al. | 607/40 |
| 2003/0088189 | A1 | 5/2003 | Tu et al. | 600/549 |
| 2003/0130711 | A1 | 7/2003 | Pearson et al. | |
| 2003/0170898 | A1 | 9/2003 | Gundersen et al. | |
| 2003/0208200 | A1 | 11/2003 | Palanker et al. | |
| 2003/0225360 | A1 | 12/2003 | Eppstein et al. | |
| 2004/0019371 | A1 | 1/2004 | Jaafar et al. | |
| 2004/0059389 | A1* | 3/2004 | Chornenky et al. | 607/3 |
| 2004/0146877 | A1 | 7/2004 | Diss et al. | |
| 2004/0153057 | A1 | 8/2004 | Davison | |
| 2004/0243107 | A1 | 12/2004 | Mackoviak et al. | |
| 2004/0267189 | A1 | 12/2004 | Mavor et al. | |
| 2005/0043726 | A1 | 2/2005 | McHale et al. | 606/27 |
| 2005/0049541 | A1 | 3/2005 | Behar et al. | |
| 2005/0165393 | A1 | 7/2005 | Eppstein | |
| 2005/0171523 | A1 | 8/2005 | Rubinsky et al. | |
| 2005/0171574 | A1 | 8/2005 | Rubinsky et al. | |
| 2005/0182462 | A1 | 8/2005 | Chornenky et al. | |
| 2005/0261672 | A1 | 11/2005 | Deem et al. | |
| 2005/0288730 | A1 | 12/2005 | Deem et al. | |
| 2006/0015147 | A1 | 1/2006 | Persson et al. | 607/5 |
| 2006/0025760 | A1 | 2/2006 | Podhajsky | |
| 2006/0079883 | A1 | 4/2006 | Elmouelhi et al. | |
| 2006/0121610 | A1 | 6/2006 | Rubinsky et al. | |
| 2006/0212078 | A1 | 9/2006 | Demarais et al. | |
| 2006/0217703 | A1* | 9/2006 | Chornenky et al. | 606/41 |
| 2006/0264752 | A1 | 11/2006 | Rubinsky et al. | |
| 2007/0043345 | A1 | 2/2007 | Davalos et al. | |
| 2007/0118069 | A1 | 5/2007 | Persson et al. | 604/20 |
| 2008/0052786 | A1* | 2/2008 | Lin et al. | 800/10 |

FOREIGN PATENT DOCUMENTS

| | | |
|---|---|---|
| DE | 4000893 | 7/1991 |
| EP | 0378132 | 7/1990 |
| EP | 0 935 482 B1 | 5/2005 |
| EP | 0935482 | 5/2005 |
| WO | 9639531 | 12/1996 |
| WO | 0020554 | 4/2000 |
| WO | 0107583 | 2/2001 |
| WO | 0107584 | 2/2001 |
| WO | 0107585 | 2/2001 |
| WO | 0181533 | 11/2001 |
| WO | 2004037341 | 5/2004 |

OTHER PUBLICATIONS

S.B. Dev, et al., "Medical Applications of Electroporation", IEEE Transactions of Plasma Science, vol. 28, No. 1, pp. 206-223, Feb. 2000.

E. Neumann, et al., "Permeability Changes Induced by Electric Impulses in Vesicular Membranes", J. Membrane Biol., vol. 10, pp. 279-290, 1972.

J.M. Crowley, "Electrical Breakdown of Biomolecular Lipid Membranes as an Electromechanical Instability", Biophysical Journal, vol. 13, pp. 711-724, 1973.

U. Zimmermann, et al., "Dielectric Breakdown of Cell Membranes", Biophysical Journal, vol. 14, No. 11, pp. 881-899, 1974.

K. Kinosita Jr., et al., "Hemolysis of Human Erythrocytes by a Transient Electric Field", Proc. Natl. Acad. Sci. USA, vol. 74, No. 5, pp. 1923-1927, 1977.

P.F. Baker, et al., "Calcium-Dependent Exocytosis in Bovine Adrenal Medullary Cells with Leaky Plasma Membranes", Nature, vol. 276, pp. 620-622, 1978.

B. Gauger, et al, "A Study of Dielectric Membrane Breakdown in the *Fucus* Egg", J. Membrane Biol., vol. 48, No. 3, pp. 249-264, 1979.

E. Neumann, et al., "Gene Transfer into Mouse Lyoma Cells by Electroporation in High Electric Fields", J. EMBO, vol. 1, No. 7, pp. 841-845, 1982.

R. Heller, et al., "Clinical Applications of Electrochemotherapy", Advanced Drug Delivery Reviews, vol. 35, pp. 119-129, 1999.

M. Okino, et al., "Effects of a High-Voltage Electrical Impulse and an Anticancer Drug on in Vivo Growing Tumors", Japenese Journal of Cancer Research, vol. 78, pp. 1319-1321, 1987.

L.M. Mir, et al, "Electrochemotherapy Potentiation of Antitumour Effect of Bleomycin by Local Electric Pulses", European Journal of Cancer, vol. 27, No. 1, pp. 68-72, 1991.

L.M. Mir, et al., "Electrochemotherapy, a Novel Antitumor Treatment: First Clinical Trial", C.R. Acad. Sci. Paris, Ser. III, vol. 313, pp. 613-618, 1991.

L.M. Mir, et al., "Therapeutic Perspectives of in vivo Cell Electropermeabilization", Bioelectrochmeistry, vol. 53, pp. 1-10, 2000.

M.J. Jaroszeski, et al., "In Vivo Gene Delivery by Electroporation", Advanced Drug Delivery Review, vol. 35, pp. 131-137, 1999.

R.V. Davalos, "Real Time Imaging for Molecular Medicine through Electrical Impedance Tomography of Electroporation", Mechanical Engineering, University of California at Berkeley, pp. 237, 2002.

L.M. Mir, et al., "Effective Treatment of Cutaneous and Subcutaneous Malignant Tumours by Electrochemotherapy", British Journal of Cancer, vol. 77, No. 12, pp. 2336-2342, 1998.

R. Davalos, et al., "Tissue Ablation with Irreversible Electroporation", Annals of Biomedical Engineering., vol. 33, No. 2, Feb. 2005.

G. Onik, et al., "Ultrasonic Characteristics of Frozen Liver", Cryobiology, vol. 21, pp. 321-328, 1984.

J.C. Gilbert, et al., "The Use of Ultrasound Imaging for Monitoring Cryosurgery", IEEE Engineering in Medicine and Biology, pp. 107-112, 1984.

G. Onik, et al., "Sonographic Monitoring of Hepatic Cryosurgery in an Experimental Animal Model", AJR American J. of Roentgenology, vol. 144, pp. 1043-1047, May 1985.

Y. Huang, et al., "Micro-Electroporation: Improving the efficiency and Understanding of Electrical Permeabilization of Cells", Biomedical Microdevices, vol. 2, No. 2, pp. 145-150, 1999.

R.V. Davalos, et al., "A Feasibility Study for Electrical impedance Tomography as a Means to Monitor Tissue Electorporation in Molecular Medicine", IEEE Transactions on Biomedical Engineering, vol. 49, No. 4, pp. 400-404, 2002.

R.V. Davalos, et al., "Theoretical Analysis of the Thermal Effects During in vivo Tissue Electroporation", Bioelectrochemistry, vol. 61, pp. 99-107, 2003.

Amasha, et al., Quantitative Assessment of Impedance Tomography for Temperature Measurements in Microwave Hyperthermia, Clin. Phys. Physiol. Meas., 1998, Suppl. A, 49-53.

Andreason, Electroporation as a Technique for the Transfer of Macromolecules into Mammalian Cell Lines, J. Tiss. Cult. Meth., 15:56-62, 1993.

Baker, et al., Calcium-Dependent Exocytosis in Bovine Adrenal Medullary Cells with Leaky Plasma Membranes, Nature, vol. 276, pp. 620-622, 1978.

Barber, Electrical Impedance Tomography Applied Potential Tomography, Advances in Biomedical Engineering, Beneken and Thevenin, eds., IOS Press, 1993.

Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.

Blad, et al., Impedance Spectra of Tumour Tissue in Comparison with Normal Tissue; a Possible Clinical Application for Electrical Impedance Tomography, Physiol. Meas. 17 (1996) A105-A115.

Bown, S.G., Phototherapy of tumors. World J. Surgery, 1983. 7: p. 700-9.

BPH Management Strategies: Improving Patient Satisfaction, Urology Times, May 2001, vol. 29, Supplement 1.

Brown, et al., Blood Flow Imaging Using Electrical Impedance Tomography, Clin. Phys. Physiol. Meas., 1992, vol. 13, Suppl. A, 175-179.

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.

Coates, C.W.,et al., "The Electrical Discharge of the Electric Eel, Electrophorous electricus," Zoologica, 1937, 22(1), pp. 1-32.

Cook, et al., ACT3: A High-Speed, High-Precision Electrical Impedance Tomograph, IEEE Transactions on Biomedical Engineering, vol. 41, No. 8, Aug. 1994.

Cowley, Good News for Boomers, Newsweek, Dec. 30, 1996/Jan. 6, 1997.

Cox, et al., Surgical Treatment of Atrial Fibrillation: A Review, Europace (2004) 5, S20-S-29.

Crowley, Electrical Breakdown of Biomolecular Lipid Membranes as an Electromechanical Instability, Biophysical Journal, vol. 13, pp. 711-724, 1973.

Davalos, et al., Tissue Ablation with Irreversible Electroporation, Annals of Biomedical Engineering, vol. 33, No. 2, Feb. 2005.

Davalos, et al., Theoretical Analysis of the Thermal Effects During In Vivo Tissue Electroporation, Bioelectrochemistry, vol. 61, pp. 99-107, 2003.

Davalos, et al., A Feasibility Study for Electrical Impedance Tomography as a Means to Monitor T issue Electroporation for Molecular Medicine, IEEE Transactions on Biomedical Engineering, vol. 49, No. 4, Apr. 2002.

Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.

Dean, Nonviral Gene Transfer to Skeletal, Smooth, and Cardiac Muscle in Living Animals, Am J. Physiol Cell Physiol 289: 233-245, 2005.

Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.

Dev, et al., Medical Applications of Electroporation, IEEE Transactions of Plasma Science, vol. 28, No. 1, pp. 206-223, Feb. 2000.

Duraiswami, et al., Boundary Element Techniques for Efficient 2-D and 3-D Electrical Impedance Tomography, Chemical Engineering Science, vol. 52, No. 13, pp. 2185-2196, 1997.

Duraiswami, et al., Efficient 2D and 3D Electrical Impedance Tomography Using Dual Reciprocity Boundary Element Techniques, Engineering Analysis with Boundary Elements 22, (1998) 13-31.

Duraiswami, et al., Solution of Electrical Impedance Tomography Equations Using Boundary Element Methods, Boundary Element Technology XII, 1997, pp. 226-237.

Edd, J., et al., In-Vivo Results of a New Focal Tissue Ablation Technique: Irreversible Electroporaton, IEEE Trans. Biomed. Eng. 53 (2006) p. 1409-1415.

Erez, et al., Controlled Destruction and Temperature Distributions in Biological Tissues Subjected to Monoactive Electrocoagulation, Transactions of the ASME: Journal of Mechanical Design, vol. 102, Feb. 1980.

Foster, R.S., et al., High-intensity focused ultrasound in the treatment of prostatic disease. Eur. Urol., 1993. 23: 44-7).

Fox, et al., Sampling Conductivity Images via MCMC, Mathematics Department, Auckland University, New Zealand, May 1997.

Gauger, et al., A Study of Dielectric Membrane Breakdown in the Fucus Egg, J. Membrane Biol., vol. 48, No. 3, pp. 249-264, 1979.

Gehl, et al., In Vivo Electroporation of Skeletal Muscle: Threshold, Efficacy and Relation to Electric Field Distribution, Biochimica et Biphysica Acta 1428, 1999, pp. 233-240.

Gençer, et al., Electrical Impedance Tomography: Induced-Current Imaging Achieved with a Multiple Coil System, IEEE Transactions on Biomedical Engineering, vol. 43, No. 2, Feb. 1996.

Gilbert, et al., Novel Electrode Designs for Electrochemotherapy, Biochimica et Biophysica Acta 1334, 1997, pp. 9-14.

Gilbert, et al., The Use of Ultrasound Imaging for Monitoring Cryosurgery, Proceedings 6th Annual Conference, IEEE Engineering in Medicine and Biology, 107-111, 1984.

Glidewell, et al., The Use of Magnetic Resonance Imaging Data and the Inclusion of Anisotropic Regions in Electrical Impedance Tomography, *Biomed, Sci. Instrum.* 1993; 29: 251-7.

Gothelf, et al., Electrochemotherapy: Results of Cancer Treatment Using Enhanced Delivery of Bleomycin by Electroporation, *Cancer Treatment Reviews* 2003: 29: 371-387.

Griffths, et al., A Dual-Frequency Electrical Impedance Tomography System, *Phys. Med. Biol.*, 1989, vol. 34, No. 10, pp. 1465-1476.

Griffiths, The Importance of Phase Measurement in Electrical Impedance Tomography, *Phys. Med. Biol.*, 1987, vol. 32, No. 11, pp. 1435-1444.

Griffiths, Tissue Spectroscopy with Electrical Impedance Tomography: Computer Simulations, *IEEE Transactions on Biomedical Engineering*, vol. 42, No. 9, Sep. 1995.

Gumerov, et al., The Dipole Approximation Method and Its Coupling with the Regular Boundary Element Method for Efficient Electrical Impedance Tomography, *Boundary Element Technology* XIII, 1999.

Hapala, Breaking the Barrier: Methods for Reversible Permeabilization of Cellular Membranes, *Critical Reviews in Biotechnology*, 17(2): 105-122, 1997.

Heller, et al., Clinical Applications of Electrochemotherapy, *Advanced Drug Delivery Reviews*, vol. 35, pp. 119-129, 1999.

Ho, et al., Electroporation of Cell Membranes: A Review, *Critical Reviews in Biotechnology*, 16(4): 349-362, 1996.

Holder, et al., Assessment and Calibration of a Low-Frequency System for Electrical Impedance Tomography (EIT), Optimized for Use in Imaging Brain Function in Ambulant Human Subjects, *Annals of the New York Academy of Science*, vol. 873, Issue 1, Electrical BI, pp. 512-519, 1999.

Huang, et al., Micro-Electroporation: Improving the Efficiency and Understanding of Electrical Permeabilization of Cells, *Biomedical Microdevices*, vol. 2, pp. 145-150, 1999.

Hughes, et al., An Analysis of Studies Comparing Electrical Impedance Tomography with X-Ray Videofluoroscopy in the Assessment of Swallowing, *Physiol. Meas.* 15, 1994, pp. A199-A209.

Issa, et al., The TUNA Procedure for BPH: Review of the Technology: The TUNA Procedure for BPH: Basic Procedure and Clinical Results, Reprinted from *Infections in Urology*, Jul./Aug. 1998 and Sep./Oct. 1998.

Ivanuša, et al., MRI Macromolecular Contrast Agents as Indicators of Changed Tumor Blood Flow, *Radiol. Oncol.* 2001; 35(2): 139-47.

Jaroszeski, et al., In Vivo Gene Delivery by Electroporation, *Advanced Drug Delivery Review*, vol. 35, pp. 131-137, 1999.

Kinosita, et al., Hemolysis of Human Erythrocytes by a Transient Electric Field, *Proc. Natl. Acad. Sci. USA*, vol. 74, No. 5, pp. 1923-1927, 1977.

Liu, et al., Measurement of Pharyngeal Transit Time by Electrical Impedance Tomography, *Clin. Phys. Physiol. Meas.*, 1992, vol. 13, Suppl. A, pp. 197-200.

Lundqvist, et al., Altering the Biochemical State of Individual Cultured Cells and Organelles with Ultramicroelectrodes, *Proc. Natl. Acad. Sci. USA,* vol. 95, pp. 10356-10360, Sep. 1998.

Lurquin, Gene Transfer by Electroporation, *Molecular Biotechnology*, vol. 7, 1997.

Lynn, et al., A New Method for the Generation and Use of Focused Ultrasound in Experimental Biology, *The Journal of General Physiology*, vol. 26, 179-193, 1942.

Miklavčič, et al., A Validated Model of an in Vivo Electric Field Distribution in Tissues for Electrochemotherapy and for DNA Electrotransfer for Gene Therapy, *Biochimica et Biophysica Acta* 1523 (2000), pp. 73-83.

Miklavčič, et al., The Importance of Electric Field Distribution for Effective in Vivo Electroporation of Tissues, *Biophysical Journal*, vol. 74, May 1998, pp. 2152-2158.

Miller, L., et al., Cancer cells ablation with irreversible electroporation, *Technology in Cancer Research and Treatment* 4 (2005) 699-706.

Mir, Therapeutic Perspectives of In Vivo Cell Electropermeabilization, *Bioelectrochemistry*, vol. 53, pp. 1-10, 2000.

Mir, L.M., et al., Electric Pulse-Mediated Gene Delivery to Various Animal Tissues, in Advances in Genetics, Academic Press, 2005, p. 83-114.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, et al., Effective Treatment of Cutaneous and Subcutaneous Malignant Tumours by Electrochemotherapy, *British Journal of Cancer*, vol. 77, No. 12, pp. 2336-2342, 1998.

Mir, et al., Electrochemotherapy Potentiation of Antitumour Effect of Bleomycin by Local Electric Pulses, *European Journal of Cancer*, vol. 27, No. 1, pp. 68-72, 1991.

Mir, et al., Electrochemotherapy, a Novel Antitumor Treatment: First Clinical Trial, *C.R. Acad. Sci. Paris*, Ser. III, vol. 313, pp. 613-618, 1991.

Narayan, et al., Establishment and Characterization of a Human Primary Prostatic Adenocarcinoma Cell Line (ND-1), *The Journal of Urology*, vol. 148, 1600-1604, Nov. 1992.

Naslund, Michael J., Transurethral Needle Ablation of the Prostate, *Urology*, vol. 50, No. 2, Aug. 1997.

Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.

Neumann, et al., Gene Transfer into Mouse Lyoma Cells by Electroporation in High Electric Fields, *J. Embo.*, vol. 1, No. 7, pp. 841-845, 1982.

Neumann, et al., Permeability Changes Induced by Electric Impulses in Vesicular Membranes, *J. Membrane Biol.*, vol. 10, pp. 279-290, 1972.

Okino, et al., Effects of High-Voltage Electrical Impulse and an Anticancer Drug on In Vivo Growing Tumors, *Japanese Journal of Cancer Research*, vol. 78, pp. 1319-1321, 1987.

Onik, et al., Sonographic Monitoring of Hepatic Cryosurgery in an Experimental Animal Model, *AJR American J. of Roentgenology*, vol. 144, pp. 1043-1047, May 1985.

Onik, et al., Ultrasonic Characteristics of Frozen Liver, *Cryobiology*, vol. 21, pp. 321-328, 1984.

Organ, L.W., Electrophysiological principles of radiofrequency lesion making, *Apply. Neurophysiol.*, 1976. 39: p. 69-76.

Piñero, et al., Apoptotic and Necrotic Cell Death Are Both Induced by Electroporation in HL60 Human Promyeloid Leukaemia Cells, *Apoptosis*, vol. 2, No. 3, 330-336, Aug. 1997.

Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115-121.

Rubinsky, B., ed, Cryosurgery. *Annu Rev. Biomed. Eng.* vol. 2 2000. 157-187.

Sersa, et al., Reduced Blood Flow and Oxygenation in SA-1 Tumours after Electrochemotherapy with Cisplatin, *British Journal of Cancer*, 87, 1047-1054, 2002.

Sersa, et al., Tumour Blood Flow Modifying Effects of Electrochemotherapy: a Potential Vascular Targeted Mechanism, *Radiol. Oncol.*, 37(1): 43-8, 2003.

Sharma, et al., Poloxamer 188 Decreases Susceptibility of Artificial Lipid Membranes to Electroporation, *Biophysical Journal*, vol. 71, No. 6, pp. 3229-3241, Dec. 1996.

Shiina, S., et al, Percutaneous ethanol injection therapy for hepatocellular carcinoma: results in 146 patients. *AJR*, 1993, 160: p. 1023-8.

Thompson, et al., To determine whether the temperature of 2% lignocaine gel affects the initial discomfort which may be associated with its instillation into the male urethra, *BJU International* (1999), 84, 1035-1037.

Weaver, Electroporation: A General Phenomenon for Manipulating Cells and Tissues, *Journal of Cellular Biochemistry*, 51: 426-435, 1993.

Weaver, et al., Theory of Electroporation: A Review, *Bioelectrochemistry and Bioenergetics*, vol. 41, pp. 136-160, 1996.

Zimmermann, et al., Dielectric Breakdown of Cell Membranes, *Biophysical Journal*, vol. 14, No. 11, pp. 881-899, 1974.

Zlotta, et al., Possible Mechanisms of Action of Transurethral Needle Ablation of the Prostate on Benign Prostatic Hyperplasia Symptoms:

a Neurohistochemical Study, Reprinted from *Journal of Urology,* vol. 157, No. 3, Mar. 1997, pp. 894-899.

Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

* cited by examiner

METHODS AND SYSTEMS FOR TREATING BPH USING ELECTROPORATION

CROSS-REFERENCE TO RELATED APPLICATIONS

This application is related to U.S. Ser. Nos. 11/165,961, 11/165,881, and 11/165,908, filed on the same date as the instant application, all of which applications are fully incorporated herein by reference.

BACKGROUND

1. Field of the Invention

This invention relates generally to electroporation, and more particularly to systems and methods for treating BPH tissue sites of a patient using electroporation.

2. Description of the Related Art

Electroporation is defined as the phenomenon that makes cell membranes permeable by exposing them to certain electric pulses (Weaver, J. C. and Y. A. Chizmadzhev, *Theory of electroporation: a review*. Bioelectrochem. Bioenerg., 1996. 41: p. 135-60). The permeabilization of the membrane can be reversible or irreversible as a function of the electrical parameters used. In reversible electroporation the cell membrane reseals a certain time after the pulses cease and the cell survives. In irreversible electroporation the cell membrane does not reseal and the cell lyses. (Dev, S. B., Rabussay, D. P., Widera, G., Hofmann, G. A., *Medical applications of electroporation*, IEEE Transactions of Plasma Science, Vol 28 No 1, February 2000, pp 206-223).

Dielectric breakdown of the cell membrane due to an induced electric field, irreversible electroporation, was first observed in the early 1970s (Neumann, E. and K. Rosenheck, *Permeability changes induced by electric impulses in vesicular membranes*. J. Membrane Biol., 1972. 10: p. 279-290; Crowley, J. M., *Electrical breakdown of biomolecular lipid membranes as an electromechanical instability*. Biophysical Journal, 1973. 13: p. 711-724; Zimmermann, U., J. Vienken, and G. Pilwat, *Dielectric breakdown of cell membranes*. Biophysical Journal, 1974. 14(11): p. 881-899). The ability of the membrane to reseal, reversible electroporation, was discovered separately during the late 1970s (Kinosita Jr, K. and T. Y. Tsong, *Hemolysis of human erythrocytes by a transient electric field*. Proc. Natl. Acad. Sci. USA, 1977. 74(5): p. 1923-1927; Baker, P. F. and D. E. Knight, *Calcium-dependent exocytosis in bovine adrenal medullary cells with leaky plasma membranes*. Nature, 1978. 276: p. 620-622; Gauger, B. and F. W. Bentrup, *A Study of Dielectric Membrane Breakdown in the Fucus Egg*. J. Membrane Biol., 1979. 48(3): p. 249-264).

The mechanism of electroporation is not yet fully understood. It is thought that the electrical field changes the electrochemical potential around a cell membrane and induces instabilities in the polarized cell membrane lipid bilayer. The unstable membrane then alters its shape forming aqueous pathways that possibly are nano-scale pores through the membrane, hence the term "electroporation" (Chang, D. C., et al., *Guide to Electroporation and Electrofusion*. 1992, San Diego, Calif.: Academic Press, Inc.). Mass transfer can now occur through these channels under electrochemical control. Whatever the mechanism through which the cell membrane becomes permeabilized, electroporation has become an important method for enhanced mass transfer across the cell membrane.

The first important application of the cell membrane permeabilizing properties of electroporation is due to Neumann (Neumann, E., et al., *Gene transfer into mouse lyoma cells by electroporation in high electric fields*. J. EMBO, 1982. 1: p. 841-5). He has shown that by applying reversible electroporation to cells it is possible to sufficiently permeabilize the cell membrane so that genes, which are macromolecules that normally are too large to enter cells, can after electroporation enter the cell. Using reversible electroporation electrical parameters is crucial to the success of the procedure, since the goal of the procedure is to have a viable cell that incorporates the gene.

Following this discovery electroporation became commonly used to reversible permeabilize the cell membrane for various applications in medicine and biotechnology to introduce into cells or to extract from cells chemical species that normally do not pass, or have difficulty passing across the cell membrane, from small molecules such as fluorescent dyes, drugs and radioactive tracers to high molecular weight molecules such as antibodies, enzymes, nucleic acids, HMW dextrans and DNA.

Following work on cells outside the body, reversible electroporation began to be used for permeabilization of cells in tissue. Heller, R., R. Gilbert, and M. J. Jaroszeski, *Clinical applications of electrochemotherapy*. Advanced drug delivery reviews, 1999. 35: p. 119-129. Tissue electroporation is now becoming an increasingly popular minimally invasive surgical technique for introducing small drugs and macromolecules into cells in specific areas of the body. This technique is accomplished by injecting drugs or macromolecules into the affected area and placing electrodes into or around the targeted tissue to generate reversible permeabilizing electric field in the tissue, thereby introducing the drugs or macromolecules into the cells of the affected area (Mir, L. M., *Therapeutic perspectives of in vivo cell electropermeabilization*. Bioelectrochemistry, 2001. 53: p. 1-10).

The use of electroporation to ablate undesirable tissue was introduced by Okino and Mohri in 1987 and Mir et al. in 1991. They have recognized that there are drugs for treatment of cancer, such as bleomycin and cys-platinum, which are very effective in ablation of cancer cells but have difficulties penetrating the cell membrane. Furthermore, some of these drugs, such as bleomycin, have the ability to selectively affect cancerous cells which reproduce without affecting normal cells that do not reproduce. Okino and Mori and Mir et al. separately discovered that combining the electric pulses with an impermeant anticancer drug greatly enhanced the effectiveness of the treatment with that drug (Okino, M. and H. Mohri, *Effects of a high-voltage electrical impulse and an anticancer drug on in vivo growing tumors*. Japanese Journal of Cancer Research, 1987. 78(12): p. 1319-21; Mir, L. M., et al., *Electrochemotherapy potentiation of antitumour effect of bleomycin by local electric pulses*. European Journal of Cancer, 1991. 27: p. 68-72). Mir et al. soon followed with clinical trials that have shown promising results and coined the treatment electrochemotherapy (Mir, L. M., et al., *Electrochemotherapy, a novel antitumor treatment: first clinical trial*. C. R. Acad. Sci., 1991. Ser. III 313(613-8)).

Currently, the primary therapeutic in vivo applications of electroporation are antitumor electrochemotherapy (ECT), which combines a cytotoxic nonpermeant drug with permeabilizing electric pulses and electrogenetherapy (EGT) as a form of non-viral gene therapy, and transdermal drug delivery (Mir, L. M., *Therapeutic perspectives of in vivo cell electropermeabilization*. Bioelectrochemistry, 2001. 53: p. 1-10). The studies on electrochemotherapy and electrogenetherapy have been recently summarized in several publications (Jaroszeski, M. J., et al., *In vivo gene delivery by electroporation*. Advanced applications of electrochemistry, 1999. 35: p. 131-

137; Heller, R., R. Gilbert, and M. J. Jaroszeski, *Clinical applications of electrochemotherapy*. Advanced drug delivery reviews, 1999. 35: p. 119-129; Mir, L. M., *Therapeutic perspectives of in vivo cell electropermeabilization*. Bioelectrochemistry, 2001. 53: p. 1-10; Davalos, R. V., *Real Time Imaging for Molecular Medicine through electrical Impedance Tomography of Electroporation*, in *Mechanical Engineering*. 2002, University of California at Berkeley: Berkeley. p. 237). A recent article summarized the results from clinical trials performed in five cancer research centers. Basal cell carcinoma, malignant melanoma, adenocarcinoma and head and neck squamous cell carcinoma were treated for a total of 291 tumors (Mir, L. M., et al., *Effective treatment of cutaneous and subcutaneous malignant tumours by electrochemotherapy*. British Journal of Cancer, 1998. 77(12): p. 2336-2342).

Electrochemotherapy is a promising minimally invasive surgical technique to locally ablate tissue and treat tumors regardless of their histological type with minimal adverse side effects and a high response rate (Dev, S. B., et al., *Medical Applications of Electroporation*. IEEE Transactions on Plasma Science, 2000. 28(1): p. 206-223; Heller, R., R. Gilbert, and M. J. Jaroszeski, *Clinical applications of electrochemotherapy*. Advanced drug delivery reviews, 1999. 35: p. 119-129). Electrochemotherapy, which is performed through the insertion of electrodes into the undesirable tissue, the injection of cytotoxic dugs in the tissue and the application of reversible electroporation parameters, benefits from the ease of application of both high temperature treatment therapies and non-selective chemical therapies and results in outcomes comparable of both high temperature therapies and non-selective chemical therapies.

Irreversible electroporation, the application of electrical pulses which induce irreversible electroporation in cells is also considered for tissue ablation (Davalos, R. V., *Real Time Imaging for Molecular Medicine through electrical Impedance Tomography of Electroporation*, in *Mechanical Engineering*. 2002, PhD Thesis, University of California at Berkeley: Berkeley, Davalos, R., L. Mir, Rubinsky B., "*Tissue ablation with irreversible electroporation*" in print February 2005 *Annals of Biomedical Eng*,). Irreversible electroporation has the potential for becoming and important minimally invasive surgical technique. However, when used deep in the body, as opposed to the outer surface or in the vicinity of the outer surface of the body, it has a drawback that is typical to all minimally invasive surgical techniques that occur deep in the body, it cannot be closely monitored and controlled. In order for irreversible electroporation to become a routine technique in tissue ablation, it needs to be controllable with immediate feedback. This is necessary to ensure that the targeted areas have been appropriately treated without affecting the surrounding tissue. This invention provides a solution to this problem in the form of medical imaging.

Medical imaging has become an essential aspect of minimally and non-invasive surgery since it was introduced in the early 1980's by the group of Onik and Rubinsky (G. Onik, C. Cooper, H. I. Goldenberg, A. A. Moss, B. Rubinsky, and M. Christianson, "*Ultrasonic Characteristics of Frozen Liver,*" *Cryobiology*, 21, pp. 321-328, 1984, J. C. Gilbert, G. M. Onik, W Haddick, and B. Rubinsky, "*The Use of Ultrasound Imaging for Monitoring Cryosurgery,*" Proceedings 6th Annual Conference, IEEE Engineering in Medicine and Biology, 107-112, 1984 G. Onik, J. Gilbert, W. K. Haddick, R. A. Filly, P. W. Collen, B. Rubinsky, and L. Farrel, "*Sonographic Monitoring of Hepatic Cryosurgery, Experimental Animal Model,*" *American J. of Roentgenology*, May 1985, pp. 1043-1047.) Medical imaging involves the production of a map of various physical properties of tissue, which the imaging technique uses to generate a distribution. For example, in using x-rays a map of the x-ray absorption characteristics of various tissues is produced, in ultrasound a map of the pressure wave reflection characteristics of the tissue is produced, in magnetic resonance imaging a map of proton density is produced, in light imaging a map of either photon scattering or absorption characteristics of tissue is produced, in electrical impedance tomography or induction impedance tomography or microwave tomography a map of electrical impedance is produced.

Minimally invasive surgery involves causing desirable changes in tissue, by minimally invasive means. Often minimally invasive surgery is used for the ablation of certain undesirable tissues by various means. For instance in cryosurgery the undesirable tissue is frozen, in radio-frequency ablation, focused ultrasound, electrical and micro-waves hyperthermia tissue is heated, in alcohol ablation proteins are denaturized, in laser ablation photons are delivered to elevate the energy of electrons. In order for imaging to detect and monitor the effects of minimally invasive surgery, these should produce changes in the physical properties that the imaging technique monitors.

The formation of nanopores in the cell membrane has the effect of changing the electrical impedance properties of the cell (Huang, Y, Rubinsky, B., "*Micro-electroporation: improving the efficiency and understanding of electrical permeabilization of cells*" Biomedical Microdevices, Vo 3, 145-150, 2000. (Discussed in "*Nature Biotechnology*" Vol 18. pp 368, April 2000), B. Rubinsky, Y Huang. "Controlled electroporation and mass transfer across cell membranes U.S. Pat. No. 6,300,108, Oct. 9, 2001).

Thereafter, electrical impedance tomography was developed, which is an imaging technique that maps the electrical properties of tissue. This concept was proven with experimental and analytical studies (Davalos, R. V., Rubinsky, B., Otten, D. M., "*A feasibility study for electrical impedance tomography as a means to monitor tissue electroporation in molecular medicine*" IEEE Trans of Biomedical Engineering. Vol. 49, No. 4 pp 400-404, 2002, B. Rubinsky, Y. Huang. "Electrical Impedance Tomography to control electroporation" U.S. Pat. No. 6,387,671, May 14, 2002.)

There is a need for improved systems and methods for treating BPH using electroporation.

SUMMARY OF THE INVENTION

Accordingly, an object of the present invention is to provide improved systems and methods for treating BPH tissue sites using electroporation.

Another object of the present invention is to provide systems and method for treating BPH tissue sites using electroporation using sufficient electrical pulses to induce electroporation of cells in the BPH tissue site, without creating a thermal damage effect to a majority of the BPH tissue site.

Yet another object of the present invention is to provide systems and methods for treating BPH tissue sites using electroporation with real time monitoring.

A further object of the present invention is to provide systems and methods for treating BPH tissue sites using electroporation where the electroporation is performed in a controlled manner with monitoring of electrical impedance;

Still a further object of the present invention is to provide systems and methods for treating BPH tissue sites using electroporation that is performed in a controlled manner, with controlled intensity and duration of voltage.

Another object of the present invention is to provide systems and methods for treating BPH tissue sites using electroporation that is performed in a controlled manner, with a proper selection of voltage magnitude.

Yet another object of the present invention is to provide systems and methods for treating BPH tissue sites using electroporation that is performed in a controlled manner, with a proper selection of voltage application time.

A further object of the present invention is to provide systems and methods for treating BPH tissue sites using electroporation, and a monitoring electrode configured to measure a test voltage delivered to cells in the BPH tissue site and remote sites such as the rectum and the urethra.

Still a further object of the present invention is to provide systems and methods for treating BPH tissue sites using electroporation that is performed in a controlled manner to provide for controlled pore formation in cell membranes.

Still another object of the present invention is to provide systems and methods for treating BPH tissue sites using electroporation that is performed in a controlled manner to create a tissue effect in the cells at the BPH tissue site while preserving surrounding tissue.

Another object of the present invention is to provide systems and methods for treating BPH tissue sites using electroporation, and detecting an onset of electroporation of cells at the BPH tissue site.

Yet another object of the present invention is to provide systems and methods for treating BPH tissue sites using electroporation where the electroporation is performed in a manner for modification and control of mass transfer across cell membranes.

A further object of the present invention is to provide systems and methods for treating BPH tissue sites using electroporation, and an array of electrodes that creates a boundary around the BPH tissue site to produce a volumetric cell necrosis region.

These and other objects of the present invention are achieved in, a system for treating benign prostate hyperplasia (BPH) of a prostate. At least first and second mono-polar electrodes are configured to be introduced at or near a BPH tissue site of the prostate gland of the patient. A voltage pulse generator is coupled to the first and second mono-polar electrodes. The voltage pulse generator is configured to apply sufficient electrical pulses between the first and second mono-polar electrodes to induce electroporation of cells in the BPH tissue site, to create necrosis of cells of the BPH tissue site, but insufficient to create a thermal damaging effect to a majority of the BPH tissue site.

In another embodiment of the present invention, a system for treating BPH of a prostate is provided. A bipolar electrode is configured to be introduced at or near a BPH tissue site of the prostate gland of the patient. A voltage pulse generator is coupled to the bipolar electrode. The voltage pulse generator is configured to apply sufficient electrical pulses to the bipolar electrode to induce electroporation of cells in the BPH tissue site, to create necrosis of cells of the BPH tissue site, but insufficient to create a thermal damaging effect to a majority of the BPH tissue site.

In another embodiment of the present invention, a method is provided for treating BPH of a prostate. At least first and second mono-polar electrodes are introduced to a BPH tissue site of a patient. The at least first and second mono-polar electrodes are positioned at or near the BPH tissue site. An electric field is applied in a controlled manner to the BPH tissue site. The electric field is sufficient to produce electroporation of cells at the BPH tissue site, and below an amount that causes thermal damage to a majority of the BPH tissue site.

In another embodiment of the present invention, a method is provided for treating BPH of a prostate. A bipolar electrode is introduced to a BPH tissue site of a patient. The bipolar electrode is positioned at or near the BPH tissue site. An electric field is applied in a controlled manner to the BPH tissue site. The electric field is sufficient to produce electroporation of cells at the BPH tissue site, and below an amount that causes thermal damage to a majority of the BPH tissue site.

DETAILED DESCRIPTION

Definitions

The term "reversible electroporation" encompasses permeabilization of a cell membrane through the application of electrical pulses across the cell. In "reversible electroporation" the permeabilization of the cell membrane ceases after the application of the pulse and the cell membrane permeability reverts to normal or at least to a level such that the cell is viable. Thus, the cell survives "reversible electroporation." It may be used as a means for introducing chemicals, DNA, or other materials into cells.

The term "irreversible electroporation" also encompasses the permeabilization of a cell membrane through the application of electrical pulses across the cell. However, in "irreversible electroporation" the permeabilization of the cell membrane does not cease after the application of the pulse and the cell membrane permeability does not revert to normal and as such cell is not viable. Thus, the cell does not survive "irreversible electroporation" and the cell death is caused by the disruption of the cell membrane and not merely by internal perturbation of cellular components. Openings in the cell membrane are created and/or expanded in size resulting in a fatal disruption in the normal controlled flow of material across the cell membrane. The cell membrane is highly specialized in its ability to regulate what leaves and enters the cell. Irreversible electroporation destroys that ability to regulate in a manner such that the cell can not compensate and as such the cell dies.

"Ultrasound" is a method used to image tissue in which pressure waves are sent into the tissue using a piezoelectric crystal. The resulting returning waves caused by tissue reflection are transformed into an image.

"MRI" is an imaging modality that uses the perturbation of hydrogen molecules caused by a radio pulse to create an image.

"CT" is an imaging modality that uses the attenuation of an x-ray beam to create an image.

"Light imaging" is an imaging method in which electromagnetic waves with frequencies in the range of visible to far infrared are send into tissue and the tissue's reflection and/or absorption characteristics are reconstructed.

"Electrical impedance tomography" is an imaging technique in which a tissue's electrical impedance characteristics are reconstructed by applying a current across the tissue and measuring electrical currents and potentials In accordance with the present invention specific imaging technologies used in the field of medicine are used to create images of tissue affected by electroporation pulses. The images are created during the process of carrying out irreversible electroporation and are used to focus the electroporation on tissue to be ablated and to avoid ablating tissue such as nerves. The process of the invention may be carried out by placing electrodes, such as a needle electrode in the imaging path of an imaging device. When the electrodes are activated the image device creates an image of tissue being subjected to electroporation. The effectiveness and extent of the electroporation over a given area of tissue can be determined in real time using the imaging technology.

Reversible electroporation requires electrical parameters in a precise range of values that induce only reversible electroporation. To accomplish this precise and relatively narrow range of values (between the onset of electroporation and the onset of irreversible electroporation) when reversible electroporation devices are designed they are designed to generally operate in pairs or in a precisely controlled configuration that allows delivery of these precise pulses limited by certain upper and lower values. In contrast, in irreversible electroporation the limit is more focused on the lower value of the pulse which should be high enough to induce irreversible electroporation.

Higher values can be used provided they do not induce burning. Therefore the design principles are such that no matter how many electrodes are use the only constrain is that the electrical parameters between the most distant ones be at least the value of irreversible electroporation. If within the electroporated regions and within electrodes there are higher gradients this does not diminish the effectiveness of the probe. From these principles we can use a very effective design in which any irregular region to be ablated can be treated by surrounding the region with ground electrodes and providing the electrical pulses from a central electrode. The use of the ground electrodes around the treated area has another potential value—it protects the tissue outside the area that is intended to be treated from electrical currents and is an important safety measure. In principle, to further protect an area of tissue from stray currents it would be possible to put two layers of ground electrodes around the area to be ablated. It should be emphasized that the electrodes can be infinitely long and can also be curves to better hug the undesirable area to be ablated.

In one embodiment of the present invention, methods are provided to apply an electrical pulse or pulses to BPH tissue sites. The pulses are applied between electrodes and are applied in numbers with currents so as to result in irreversible electroporation of the cells without damaging surrounding cells. Energy waves are emitted from an imaging device such that the energy waves of the imaging device pass through the area positioned between the electrodes and the irreversible electroporation of the cells effects the energy waves of the imaging device in a manner so as to create an image.

Typical values for pulse length for irreversible electroporation are in a range of from about 5 microseconds to about 62,000 milliseconds or about 75 microseconds to about 20,000 milliseconds or about 100 microseconds±10 microseconds. This is significantly longer than the pulse length generally used in intracellular (nano-seconds) electro-manipulation which is 1 microsecond or less—see published U.S. application 2002/0010491 published Jan. 24, 2002. Pulse lengths can be adjusted based on the real time imaging.

The pulse is at voltage of about 100 V/cm to 7,000 V/cm or 200 V/cm to 2000 V/cm or 300V/cm to 1000 V/cm about 600 V/cm±10% for irreversible electroporation. This is substantially lower than that used for intracellular electro-manipulation which is about 10,000 V/cm, see U.S. application 2002/0010491 published Jan. 24, 2002. The voltage can be adjusted alone or with the pulse length based on real time imaging information.

The voltage expressed above is the voltage gradient (voltage per centimeter). The electrodes may be different shapes and sizes and be positioned at different distances from each other. The shape may be circular, oval, square, rectangular or irregular etc. The distance of one electrode to another may be 0.5 to 10 cm., 1 to 5 cm., or 2-3 cm. The electrode may have a surface area of 0.1-5 sq. cm. or 1-2 sq. cm.

The size, shape and distances of the electrodes can vary and such can change the voltage and pulse duration used and can be adjusted based on imaging information. Those skilled in the art will adjust the parameters in accordance with this disclosure and imaging to obtain the desired degree of electroporation and avoid thermal damage to surrounding cells.

Thermal effects require electrical pulses that are substantially longer from those used in irreversible electroporation (Davalos, R. V., B. Rubinsky, and L. M. Mir, *Theoretical analysis of the thermal effects during in vivo tissue electroporation.* Bioelectrochemistry, 2003. Vol 61(1-2): p. 99-107). When using irreversible electroporation for tissue ablation, there may be concern that the irreversible electroporation pulses will be as large as to cause thermal damaging effects to the surrounding tissue and the extent of the BPH tissue site ablated by irreversible electroporation will not be significant relative to that ablated by thermal effects. Under such circumstances irreversible electroporation could not be considered as an effective BPH tissue site ablation modality as it will act in superposition with thermal ablation. To a degree, this problem is addressed via the present invention using imaging technology.

In one aspect of the invention the imaging device is any medical imaging device including ultrasound, X-ray technologies, magnetic resonance imaging (MRI), light imaging, electrical impedance tomography, electrical induction impedance tomography and microwave tomography. It is possible to use combinations of different imaging technologies at different points in the process.

For example, one type of imaging technology can be used to precisely locate a BPH tissue site, a second type of imaging technology can be used to confirm the placement of electrodes relative to the BPH tissue site. And yet another type of imaging technology could be used to create images of the currents of irreversible electroporation in real time. Thus, for example, MRI technology could be used to precisely locate the BPH tissue site. Electrodes could be placed and identified as being well positioned using X-ray imaging technologies. Current could be applied to carry out irreversible electroporation while using ultrasound technology to determine the extent of BPH tissue site effected by the electroporation pulses. It has been found that within the resolution of calculations and imaging the extent of the image created on ultrasound corresponds to an area calculated to be irreversibly electroporated. Within the resolution of histology the image created by the ultrasound image corresponds to the extent of BPH tissue site ablated as examined histologically.

Because the effectiveness of the irreversible electroporation can be immediately verified with the imaging it is possible to limit the amount of unwanted damage to surrounding tissues and limit the amount of electroporation that is carried out. Further, by using the imaging technology it is possible to reposition the electrodes during the process. The electrode repositioning may be carried out once, twice or a plurality of times as needed in order to obtain the desired degree of irreversible electroporation on the desired BPH tissue site.

In accordance with one embodiment of the present invention, a method may be carried out which comprises several steps. In a first step an area of BPH tissue site to be treated by irreversible electroporation is imaged. Electrodes are then placed in the BPH tissue site with the BPH tissue site to be ablated being positioned between the electrodes. Imaging can also be carried out at this point to confirm that the electrodes are properly placed. After the electrodes are properly placed pulses of current are run between the two electrodes and the pulsing current is designed so as to minimize damage to surrounding tissue and achieve the desired irreversible electroporation of the BPH tissue site. While the irreversible electroporation is being carried out imaging technology is used and that imaging technology images the irreversible electroporation occurring in real time. While this is occurring the amount of current and number of pulses may be adjusted so as to achieve the desired degree of electroporation. Further, one or more of the electrodes may be repositioned so as to make it possible to target the irreversible electroporation and ablate the desired BPH tissue site.

Figure 1:
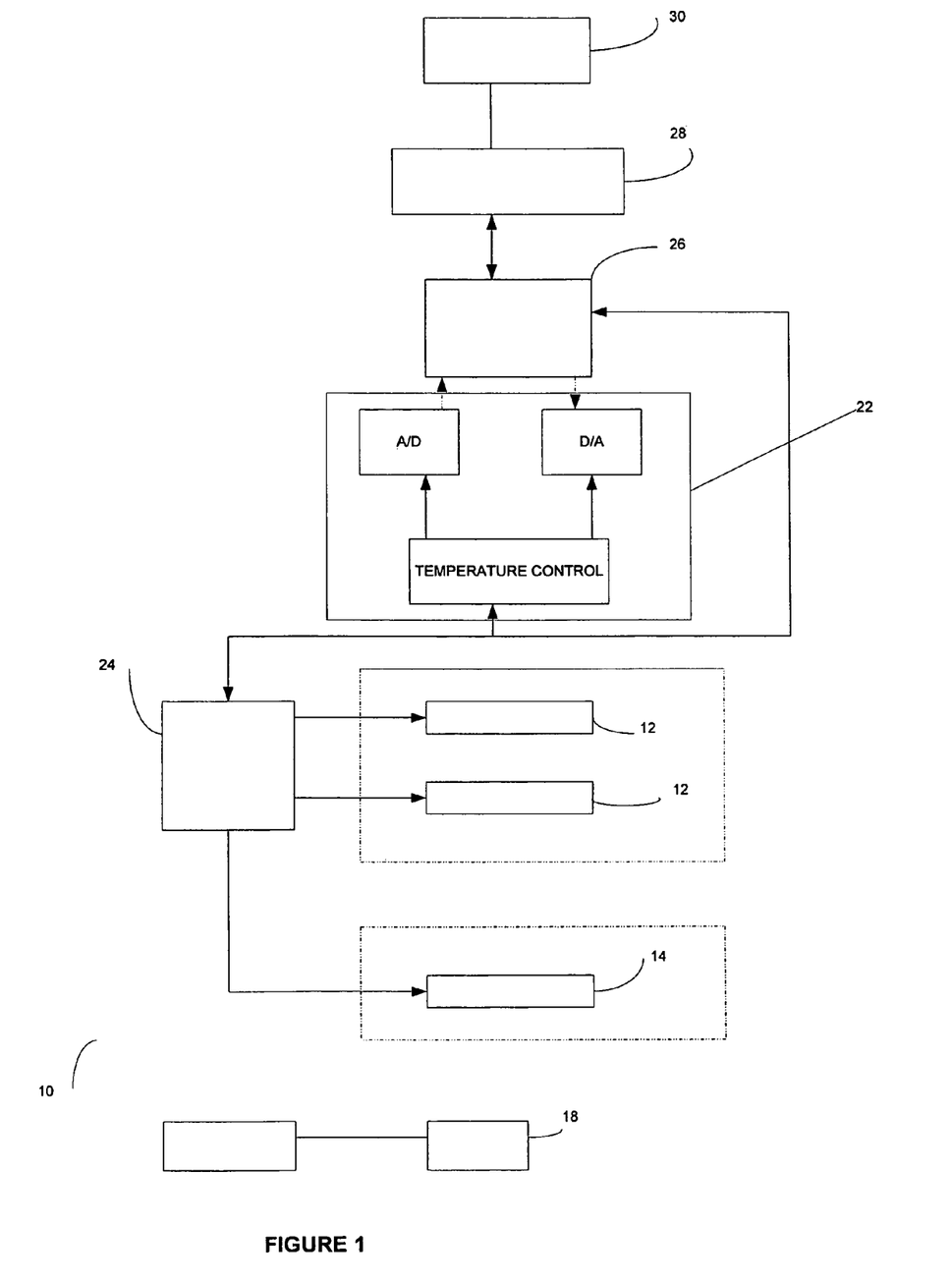
FIG. 1 illustrates a schematic diagram for one embodiment of a electroporation system of the present invention.

Referring to FIG. 1, one embodiment of the present invention provides a system, generally denoted as 10, for treating a BPH tissue site of a patient.

Two or more monopolar electrodes 12, one or more bipolar electrodes 14 or an array 16 of electrodes can be utilized, as illustrated in FIGS. 2(a)-2(d). In one embodiment, at least first and second monopolar electrodes 12 are configured to be introduced at or near the BPH tissue site of the patient. It will be appreciated that three or more monopolar electrodes 12 can be utilized. The array 16 of electrodes is configured to be in a substantially surrounding relationship to the BPH tissue site. The array 16 of electrodes can employ a template 17 to position and/or retain each of the electrodes. Template 17 can maintain a geometry of the array 16 of electrodes. Electrode placement and depth can be determined by the physician. The monopolar and bi-polar electrodes 12 and 14, and the array 16 of electrodes can be introduced through, the rectal wall, the peritoneum, urethra and the like.

Figure 3:
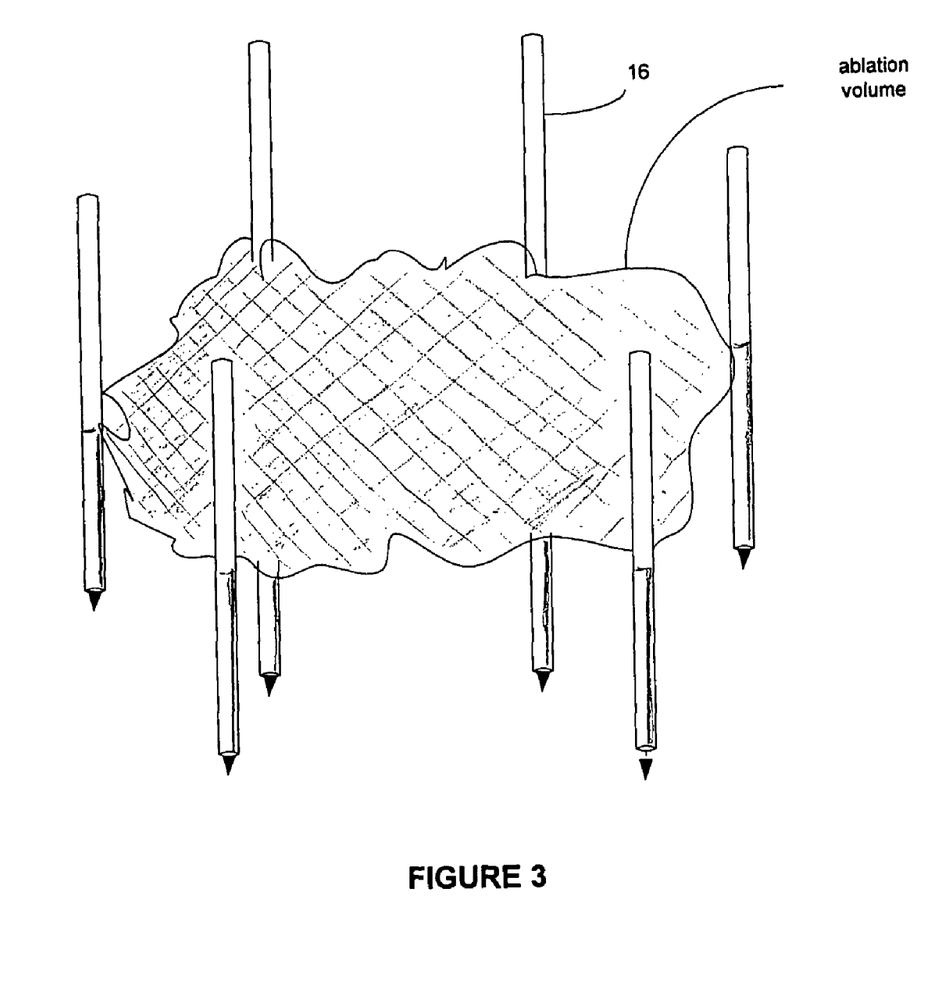
FIG. 3 illustrates one embodiment of the present invention with an array of electrodes positioned around a BPH tissue site, creating a boundary around the BPH tissue site to produce a volumetric cell necrosis region.

As shown in FIG. 3, the array 16 of electrodes creates a boundary around the BPH tissue site to produce a volumetric cell necrosis region. Essentially, the array 16 of electrodes makes a treatment area the extends from the array 16 of electrodes, and extends in an inward direction. The array 16 of electrodes can have a pre-determined geometry, and each of the associated electrodes can be deployed individually or simultaneously at the BPH tissue site either percutaneously, or planted in-situ in the patient.

Figures 2A, 2B, 2C, 2D:
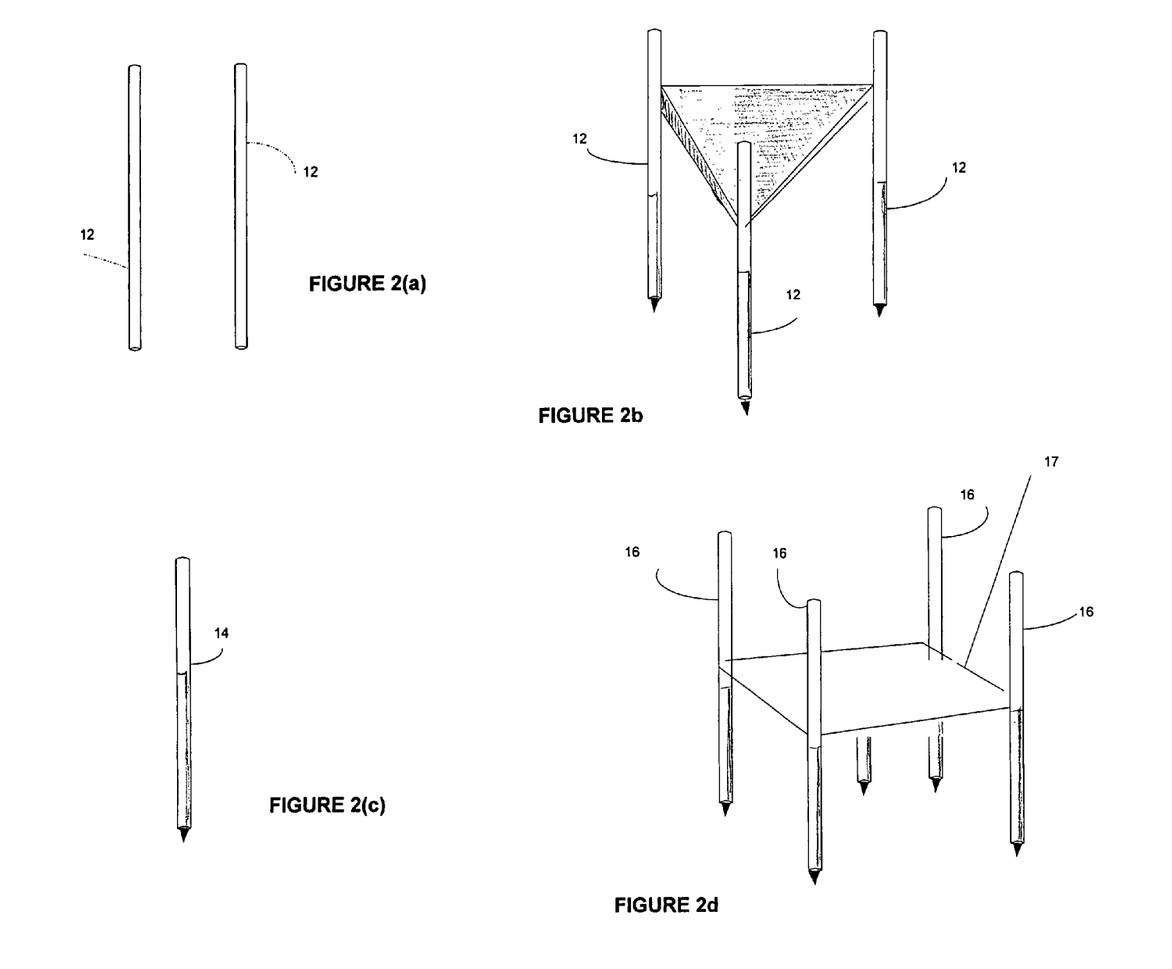
FIG. 2(a) illustrates an embodiment of the present invention with two mono-polar electrodes that can be utilized for electroporation with the FIG. 1 system.
FIG. 2(b) illustrates an embodiment of the present invention with three mono-polar electrodes that can be utilized for electroporation with the FIG. 1 system.
FIG. 2(c) illustrates an embodiment of the present invention with a single bi-polar electrode that can be utilized for electroporation with the FIG. 1 system.
FIG. 2(d) illustrates an embodiment of the present invention with an array of electrodes coupled to a template that can be utilized for electroporation with the FIG. 1 system.

In one embodiment, the monopolar electrodes 12 are separated by a distance of about 5 mm to 10 cm and they have a circular cross-sectional geometry. One or more additional probes 18 can be provided, including monitoring probes, an aspiration probe such as one used for liposuction, fluid introduction probes, and the like. Each bipolar electrode 14 can have multiple electrode bands 20. The spacing and the thickness of the electrode bands 20 is selected to optimize the shape of the electric field. In one embodiment, the spacing is about 1 mm to 5 cm typically, and the thickness of the electrode bands 20 can be from 0.5 mm to 5 cm.

Referring again to FIG. 1, a voltage pulse generator 22 is coupled to the electrodes 12, 14 and the array 16. The voltage pulse generator 22 is configured to apply sufficient electrical pulses between the first and second monopolar electrodes 12, bi-polar electrode 14 and array 16 to induce electroporation of cells in the BPH tissue site, and create necrosis of cells of the BPH tissue site. However, the applied electrical pulses are insufficient to create a thermal damaging effect to a majority of the BPH tissue site.

The electrodes 12, 14 and array 16 are each connected through cables to the voltage pulse generator 22. A switching device 24 can be included. The switching device 24, with software, provides for simultaneous or individual activation of multiple electrodes 12, 14 and array 16. The switching device 24 is coupled to the voltage pulse generator 22. In one embodiment, means are provided for individually activating the electrodes 12, 14 and array 16 in order to produce electric fields that are produced between pre-selected electrodes 12, 14 and array 16 in a selected pattern relative to the BPH tissue site. The switching of electrical signals between the individual electrodes 12, 14 and array 16 can be accomplished by a variety of different means including but not limited to, manually, mechanically, electrically, with a circuit controlled by a programmed digital computer, and the like. In one embodiment, each individual electrode 12, 14 and array 16 is individually controlled.

The pulses are applied for a duration and magnitude in order to permanently disrupt the cell membranes of cells at the BPH tissue site. A ratio of electric current through cells at the BPH tissue site to voltage across the cells can be detected, and a magnitude of applied voltage to the BPH tissue site is then adjusted in accordance with changes in the ratio of current to voltage.

In one embodiment, an onset of electroporation of cells at the BPH tissue site is detected by measuring the current. In another embodiment, monitoring the effects of electroporation on cell membranes of cells at the BPH tissue site are monitored. The monitoring can be preformed by image monitoring using ultrasound, CT scan, MRI, CT scan, and the like.

In other embodiments, the monitoring is achieved using a monitoring electrode 18. In one embodiment, the monitoring electrode 18 is a high impedance needle that can be utilized to prevent preferential current flow to a monitoring needle. The high impedance needle is positioned adjacent to or in the BPH tissue site, at a critical location. This is similar in concept and positioning as that of placing a thermocouple as in a thermal monitoring. Prior to the full electroporation pulse being delivered a "test pulse" is delivered that is some fraction of the proposed full electroporation pulse, which can be, by way of illustration and without limitation, 10%, and the like. This test pulse is preferably in a range that does not cause irreversible electroporation.

The monitoring electrode 18 measures the test voltage at the location. The voltage measured is then extrapolated back to what would be seen by the monitoring electrode 18 during the full pulse, e.g., multiplied by 10 in one embodiment, because the relationship is linear). If monitoring for a potential complication at the BPH tissue site, a voltage extrapolation that falls under the known level of irreversible electroporation indicates that the BPH tissue site where monitoring is taking place is safe. If monitoring at that BPH tissue site for adequacy of electroporation, the extrapolation falls above the known level of voltage adequate for irreversible tissue electroporation.

In one embodiment in which the bipolar electrode 14 is placed transrectally the monitoring electrode 18 is integral to the bipolar electrode 14 placed either distal or proximal to the active bipolar electrodes 14. The monitoring electrode 18 is a fixed distance form the bipolar electrode 14. In another embodiment the monitoring electrode 18 is mounted on a sheath through which the bipolar electrode 14 is placed. The distance from the bipolar electrode 14 can then be varied and positioned based on imaging and the structure to be monitored, such as the rectal mucosa. In another embodiment the monitoring electrode 18 is mounted on a biopsy guide through which the bipolar electrode 14 is placed. The monitoring electrode 18 is placed at the tip of the guide and rests against the rectal mucosa as the bipolar electrode 14 is placed.

The effects of electroporation on cell membranes of cells at the BPH tissue site can be detected by measuring the current flow.

In various embodiments, the electroporation is performed in a controlled manner, with real time monitoring, to provide for controlled pore formation in cell membranes of cells at the BPH tissue site, to create a tissue effect in the cells at the BPH tissue site while preserving surrounding tissue, with monitoring of electrical impedance, and the like.

The electroporation can be performed in a controlled manner by controlling the intensity and duration of the applied voltage and with or without real time control. Additionally, the electroporation is performed in a manner to provide for modification and control of mass transfer across cell membranes. Performance of the electroporation in the controlled manner can be achieved by selection of a proper selection of voltage magnitude, proper selection of voltage application time, and the like.

The system 10 can include a control board 26 that functions to control temperature of the BPH tissue site. In one embodiment of the present invention, the control board 26 receives its program from a controller. Programming can be in computer languages such as C or BASIC (registered trade mark) if a personnel computer is used for a controller 28 or assembly language if a microprocessor is used for the controller 28. A user specified control of temperature can be programmed in the controller 28.

The controller 28 can include a computer, a digital or analog processing apparatus, programmable logic array, a hardwired logic circuit, an application specific integrated circuit ("ASIC"), or other suitable device. In one embodiment, the controller 28 includes a microprocessor accompanied by appropriate RAM and ROM modules, as desired. The controller 28 can be coupled to a user interface 30 for exchanging data with a user. The user can operate the user interface 30 to input a desired pulsing pattern and corresponding temperature profile to be applied to the electrodes 12, 14 and array 16.

By way of illustration, the user interface 30 can include an alphanumeric keypad, touch screen, computer mouse, push-buttons and/or toggle switches, or another suitable component to receive input from a human user. The user interface 30 can also include a CRT screen, LED screen, LCD screen, liquid crystal display, printer, display panel, audio speaker, or another suitable component to convey data to a human user. The control board 26 can function to receive controller input and can be driven by the voltage pulse generator 22.

In various embodiment, the voltage pulse generator 22 is configured to provide that each pulse is applied for a duration of about, 5 microseconds to about 62 seconds, 90 to 110 microseconds, 100 microseconds, and the like. A variety of different number of pulses can be applied, including but not limited to, from about 1 to 15 pulses, about eight pulses of about 100 microseconds each in duration, and the like. In one embodiment, the pulses are applied to produce a voltage gradient at the BPH tissue site in a range of from about 50 volt/cm to about 8000 volt/cm.

In various embodiments, the BPH tissue site is monitored and the pulses are adjusted to maintain a temperature of, 100 degrees C. or less at the BPH tissue site, 75 degrees C. or less at the BPH tissue site, 60 degrees C. or less at the BPH tissue site, 50 degrees C. or less at the BPH tissue site, and the like. The temperature is controlled in order to minimize the occurrence of a thermal effect to the BPH tissue site. These temperatures can be controlled by adjusting the current-to-voltage ratio based on temperature.

In one embodiment of the present invention, the system 10 is utilized to treat BPH with electroporation of cells at a BPH tissue site, creating cell necrosis in the BPH tissue site around the urethra. The system 10 delivers electroporation pulses along the muscular fibers and nerves at the BPH tissue site and produces a volume of necrotic cells at the BPH tissue site around the urethra. Destruction of these nerves, that create an elevation in tension of the muscle fibers, is also achieved. The resulting necrotic tissue is removed by macrophages. The use of electroporation with the present invention results in the removal of cells at the BPH tissue site, associated nerves, and the total volume of the BPH tissue site is reduced, causing a reduction in pressure on the urethra and a relaxation of the prostate. The electroporation is controllably applied to spare urethral sphincters and other tissues in the prostate, as well as in adjacent tissues and organs.

First and second mono-polar electrodes 12, or more, the bi-polar electrode 14 or the array 16 of electrodes are introduced through the rectal wall, the peritoneum or the urethra of the patient. The electroporation is positioned and monitored by image monitoring with ultrasound, CT scan, MRI, CT scan, and the like, or with a monitoring electrode 18. Each of the electrodes 12, 14 or array 16 can have insulated portions and is connected to the voltage pulse generator 22.

EXAMPLE 1

An area of the BPH tissue site is imaged. Two bi-polar electrodes 12, with sharpened distal ends, are introduced into in the BPH tissue site through the rectal wall of the patient. The area of the BPH tissue site to be ablated is positioned between the two electrodes. Imaging is used to confirm that the mono-polar electrodes are properly placed. The two mono-polar electrodes are separated by a distance of 5 mm to 10 cm at various locations of the BPH tissue site. Pulses are applied with a duration of 5 microseconds to about 62 seconds each. Monitoring is preformed using ultrasound. The BPH tissue site is monitored. In response to the monitoring, pulses are adjusted to maintain a temperature of no more than 100 degrees C. A voltage gradient at the BPH tissue site in a range of from about 50 volt/cm to about 1000 volt/cm is created. A volume of the BPH tissue site of about 1 cm by 0.5 cm undergoes cell necrosis.

EXAMPLE 2

An area of the BPH tissue site is imaged. Two mono-polar electrodes 12, are introduced into in the BPH tissue site through the urethra of the patient. The area of the BPH tissue site to be ablated is positioned between the two mono-polar electrodes 12. Imaging is used to confirm that the electrodes are properly placed. The two mono-polar electrodes 12 are separated by a distance of 5 mm to 10 cm at various locations of the BPH tissue site. Pulses are applied with a duration of about 90 to 110 microseconds each. Monitoring is performed using a CT scan. The BPH tissue site is monitored. In response to the monitoring, pulses are adjusted to maintain a temperature of no more than 75 degrees C. A voltage gradient at the BPH tissue site in a range of from about 50 volt/cm to about 5000 volt/cm is created. The BPH tissue site undergoes cell necrosis.

EXAMPLE 3

An area of the BPH tissue site is imaged. The array 16 of electrodes are introduced into in the BPH tissue site through the peritoneum of the patient. The array 16 of electrodes is positioned in a surrounding relationship to the BPH. Imaging is used to confirm that the electrodes are properly placed. Pulses are applied with a duration of about 100 microseconds each. A monitoring electrode 18 is utilized. Prior to the full electroporation pulse being delivered a test pulse is delivered that is about 10% of the proposed full electroporation pulse. The test pulse does not cause irreversible electroporation. The BPH tissue site is monitored. In response to the monitoring, pulses are adjusted to maintain a temperature of no more than 60 degrees C. A voltage gradient at the BPH tissue site in a range of from about 50 volt/cm to about 8000 volt/cm is created. The BPH tissue site undergoes cell necrosis.

EXAMPLE 4

An area of the BPH tissue site is imaged. A single bi-polar electrode 14, with a sharpened distal end, is introduced into the BPH tissue site through the rectal wall of the patient. A monitoring electrode 18 is placed at a tip of a biopsy guide and rests against the rectal mucosa when the bipolar electrode 14 is placed. Imaging is used to confirm that the bi-polar electrode 14 is properly placed. Pulses are applied with a duration of 5 microseconds to about 62 seconds each. Monitoring is preformed using ultrasound. The BPH tissue site is monitored. In response to the monitoring, pulses are adjusted to maintain a temperature of no more than 100 degrees C. A voltage gradient at the BPH tissue site in a range of from about 50 volt/cm to about 1000 volt/cm is created. The BPH tissue site undergoes cell necrosis.

EXAMPLE 5

An area of the BPH tissue site is imaged. A array 16 of electrodes is introduced into the BPH tissue site through the rectal wall of the patient, and are positioned around the BPH tissue site. Imaging is used to confirm that the array 16 of electrodes is properly placed. Pulses are applied with a duration of about 90 to 110 microseconds each. Monitoring is performed using a CT scan. The BPH tissue site is monitored. In response to the monitoring, pulses are adjusted to maintain a temperature of no more than 75 degrees C. A voltage gradient at the BPH tissue site in a range of from about 50 volt/cm to about 5000 volt/cm is created. The BPH tissue site undergoes cell necrosis.

EXAMPLE 6

An area of the BPH tissue site is imaged. The array 16 of electrodes is introduced into the BPH tissue site through the peritoneum of the patient, and positioned in a surrounding relationship to the BPH tissue site. Imaging is used to confirm that the array 16 of electrodes is properly placed. Pulses are applied with a duration of about 100 microseconds each. A monitoring electrode 18 is utilized. Prior to the full electroporation pulse being delivered a test pulse is delivered that is about 10% of the proposed full electroporation pulse. The test pulse does not cause irreversible electroporation. The BPH tissue site is monitored. In response to the monitoring, pulses are adjusted to maintain a temperature of no more than 60 degrees C. A voltage gradient at the BPH tissue site in a range of from about 50 volt/cm to about 8000 volt/cm is created. The BPH tissue site undergoes cell necrosis.

The foregoing description of embodiments of the present invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

The invention claimed is:

1. A method for treating benign prostate hyperplasia (BPH) of a prostate, comprising:
introducing a bi-polar electrode to a BPH tissue site of a patient; positioning the bi-polar electrode at or near the BPH tissue site;
using a programmed control circuit to treat the BPH tissue and to control the temperature of the BPH tissue site by applying an electric field to the BPH tissue site in an amount sufficient to produce irreversible electroporation of cells at the BPH tissue site and below an amount that causes thermal damage to a majority of the BPH tissue site.

2. The method of claim 1, further comprising: using a monitoring electrode to measure a test voltage delivered to cells in the BPH tissue site.

3. The method of claim 2, wherein the test voltage is insufficient to create irreversible electroporation.

4. The method of claim 1, wherein the bipolar electrode is introduced through a rectal wall of a patient.

5. The method of claim 4, wherein a monitoring electrode is provided.

6. The method of claim 5, wherein the monitoring electrode is placed distal or proximal to the bipolar electrode.

7. The method of claim 5, wherein the monitoring electrode is placed at a fixed distance form the bipolar electrode.

8. The method of claim 5, wherein the monitoring electrode is mounted on a sheath through which the bipolar electrode is placed.

9. The method of claim 8, wherein a distance of the monitoring electrode from the bipolar electrode is varied and positioned in response to an imaging of a monitored tissue site.

10. The method of claim 9, wherein the monitored tissue site is a rectal mucosa tissue site.

11. The method of claim 10, wherein the monitoring electrode is positioned at a biopsy guide coupled to the bipolar electrode.

12. The method of claim 11, wherein the bipolar electrode is configured to be placed through the biopsy guide.

13. The method of claim 12, wherein the monitoring electrode is placed at a tip of the biopsy guide and rests against the rectal mucosa when the bipolar electrode is placed.

14. The method of claim 1, wherein the bipolar electrode is introduced through a peritoneum of the patient.

15. The method of claim 1, further comprising: performing the electroporation in a controlled manner with real time monitoring.

16. The method of claim 1, further comprising: performing the electroporation in a controlled manner to provide for controlled pore formation in cell membranes.

17. The method of claim 1, further comprising: performing the electroporation in a controlled manner to create a tissue effect of cells at the BPH tissue site while preserving surrounding tissue.

18. The method of claim 1, further comprising: performing the electroporation in a controlled manner with monitoring of electrical impedance.

19. The method of claim 1, further comprising: detecting an onset of electroporation of cells at the BPH tissue site.

20. The method of claim 1, further comprising: performing the electroporation in a controlled manner with controlled intensity and duration of voltage.

21. The method of claim 1, further comprising: performing the electroporation in a controlled manner with real time control.

22. The method of claim 1, further comprising: performing the electroporation in a manner for modification and control of mass transfer across cell membranes.

23. The method of claim 1, further comprising: performing the electroporation in a controlled manner with a proper selection of voltage magnitude.

24. The method of claim 1, wherein the electroporation is performed in a controlled manner with a proper selection of voltage magnitude.

25. The method of claim 1, wherein the electroporation is performed in a controlled manner with a proper selection of voltage application time.

26. The method of claim 1, wherein the step of applying an electric field includes applying at least one pulse and the duration of each pulse is about 5 microseconds to about 62 seconds.

27. The method of claim 1, wherein the step of applying an electric field includes applying at least one pulse and the duration of each pulse is about 90 to 110 microseconds.

28. The method of claim 1, wherein the step of applying an electric field includes applying at least one pulse and the duration of each pulse is about 100 microseconds.

29. The method of claim 27, wherein about 1 to 15 pulses are applied.

30. The method of claim 27, wherein about eight pulses of about 100 microseconds each in duration are applied.

31. The method of claim 1, wherein pulses are applied to produce a voltage gradient at the BPH tissue site in a range of from about 50 volt/cm to about 8000 volt/cm.

32. The method of claim 1, further comprising: monitoring a temperature of the BPH tissue site; and adjusting the pulses to maintain a temperature of 100 degrees C. or less at the BPH tissue site.

33. The method of claim 1, further comprising: monitoring a temperature of the BPH tissue site; and adjusting the pulses to maintain a temperature of 75 degrees C. or less at the BPH tissue site.

34. The method of claim 1, further comprising: monitoring a temperature of the BPH tissue site; and adjusting the pulses to maintain a temperature of 60 degrees C. or less at the BPH tissue site.

35. The method of claim 1, further comprising: monitoring a temperature of the BPH tissue site; and adjusting the pulses to maintain a temperature of 50 degrees C. or less at the BPH tissue site.

36. The method of claim 1, further comprising: adjusting a current-to-voltage ratio based on temperature to maintain the BPH tissue site temperature at 100 degrees C. or less.

37. The method of claim 1, further comprising: adjusting a current-to-voltage ratio based on temperature to maintain the BPH tissue site temperature at 75 degrees C. or less.

38. The method of claim 1, further comprising: adjusting a current-to-voltage ratio based on temperature to maintain the BPH tissue site temperature at 60 degrees C. or less.

39. The method of claim 1, further comprising: adjusting a current-to-voltage ratio based on temperature to maintain the BPH tissue site temperature at 50 degrees C. or less.

40. The method of claim 1, wherein the pulses applied are of sufficient duration and magnitude to permanently disrupt cell membranes of cells at the BPH tissue site.

41. The method of claim 1, wherein a ratio of electric current through cells at the BPH tissue site to voltage across the cells is detected and a magnitude of applied voltage to the BPH tissue site is adjusted in accordance with changes in the ratio of current to voltage.

42. A method for treating benign prostate hyperplasia (BPH) of a prostate, comprising:
positioning at least one treatment electrode at or near a BPH tissue site of a patient; and
using a programmed control circuit to treat the BPH tissue and to control the temperature of the BPH tissue site by applying, through the treatment electrode, an electric field to the BPH tissue site in an amount sufficient to produce irreversible electroporation of cells at the BPH tissue site and below an amount that causes thermal damage to a majority of the BPH tissue site.

43. The method of claim 42, further comprising using a monitoring electrode to measure a test voltage delivered to cells in the BPH tissue site.

44. The method of claim 43, wherein the test voltage is insufficient to create irreversible electroporation of the cells in the BPH tissue site.

45. The method of claim 43, wherein the monitoring electrode is mounted on a sheath through which the treatment electrode is placed.

46. The method of claim 45, wherein a distance of the monitoring electrode from the treatment electrode is varied and positioned in response to an imaging of a monitored tissue site.

47. The method of claim 46, wherein:
the monitoring tissue site is a rectal mucosa tissue site; and
the monitoring electrode is positioned at a biopsy guide coupled to the treatment electrode.

48. The method of claim 47, wherein the treatment electrode is configured to be placed through the biopsy guide.

49. The method of claim 48, wherein the monitoring electrode is placed at a tip of the biopsy guide and rests against the rectal mucosa when the treatment electrode is placed.

50. The method of claim 42, wherein the treatment electrode is introduced through a peritoneum of the patient.

51. The method of claim 42, wherein the step of applying an electric field includes performing the electroporation in a controlled manner with monitoring of electrical impedance at the BPH tissue site.

52. The method of claim 42, further comprising detecting an onset of electroporation of cells at the BPH tissue site.

53. The method of claim 42, wherein the step of applying an electric field includes performing the electroporation in a controlled manner with controlled voltage intensity, controlled voltage duration or both.

54. The method of claim 42, wherein the step of applying an electric field includes applying one or more electrical pulses, and the duration of each pulse is about 5 microseconds to about 62 seconds.

55. The method of claim 42, wherein the step of applying an electric field includes applying one or more electrical pulses, and the duration of each pulse is about 90 to 110 microseconds.

56. The method of claim 42, wherein the step of applying an electric field includes applying a set of about 1 to 15 pulses.

57. The method of claim 56, wherein each pulse has a duration of about 90 to 110 microseconds.

58. The method of claim 42, wherein the step of applying an electric field includes applying a plurality of electrical pulses to produce a voltage gradient at the BPH tissue site in a range of from about 50 volt/cm to about 8000 volt/cm.

59. The method of claim 42, further comprising:
monitoring a temperature of the BPH tissue site; and
adjusting the electric field to maintain a temperature of 100 degrees C. or less at the BPH tissue site.

60. The method of claim 42, further comprising:
monitoring a temperature of the BPH tissue site; and
adjusting the electric field to maintain a temperature of 75 degrees C. or less at the BPH tissue site.

61. The method of claim 42, further comprising:
monitoring a temperature of the BPH tissue site; and
adjusting the electric field to maintain a temperature of 60 degrees C. or less at the BPH tissue site.

62. The method of claim 42, further comprising:
monitoring a temperature of the BPH tissue site; and
adjusting the electric field to maintain a temperature of 50 degrees C. or less at the BPH tissue site.

63. The method of claim 42, wherein the step of applying an electric field includes applying a plurality of electrical pulses that are of sufficient duration and magnitude to permanently electroporate the cells at the BPH tissue site.

64. The method of claim 42, further comprising:
detecting a ratio of voltage across cells at the BPH tissue site to electric current through the cells; and
adjusting a magnitude of applied voltage to the BPH tissue site in accordance with changes in the ratio of voltage to current.

65. A method for treating benign prostate hyperplasia (BPH) of a prostate, comprising:
positioning at least one treatment electrode at or near a BPH tissue site of a patient; and
using a programmed control circuit to treat the BPH tissue site and to control the temperature of the BPH tissue site by applying, through the treatment electrode, an electric field to the BPH tissue site in an amount sufficient to produce irreversible electroporation of cells at the BPH tissue site and in an amount insufficient to cause the temperature to exceed 50 degrees C. at the BPH tissue site to prevent thermal damage to a majority of the BPH tissue site.

66. The method of claim 65, further comprising using a monitoring electrode to measure a test voltage delivered to cells in the BPH tissue site.

67. The method of claim 66, wherein the test voltage is insufficient to create irreversible electroporation of the cells in the BPH tissue site.

68. The method of claim 66, wherein the monitoring electrode is mounted on a sheath through which the treatment electrode is placed.

69. The method of claim 68, wherein a distance of the monitoring electrode from the treatment electrode is varied and positioned in response to an imaging of a monitored tissue site.

70. The method of claim 69, wherein:
the monitoring tissue site is a rectal mucosa tissue site; and
the monitoring electrode is positioned at a biopsy guide coupled to the treatment electrode.

71. The method of claim 70, wherein the treatment electrode is configured to be placed through the biopsy guide.

72. The method of claim 71, wherein the monitoring electrode is placed at a tip of the biopsy guide and rests against the rectal mucosa when the treatment electrode is placed.

73. The method of claim 65, wherein the treatment electrode is introduced through a peritoneum of the patient.

74. The method of claim 65, wherein the step of applying an electric field includes performing the electroporation in a controlled manner with monitoring of electrical impedance at the BPH tissue site.

75. The method of claim 65, further comprising detecting an onset of electroporation of cells at the BPH tissue site.

76. The method of claim 65, wherein the step of applying an electric field includes performing the electroporation in a controlled manner with controlled voltage intensity, controlled voltage duration or both.

77. The method of claim 65, wherein the step of applying an electric field includes applying one or more electrical pulses, and the duration of each pulse is about 5 microseconds to about 62 seconds.

78. The method of claim 65, wherein the step of applying an electric field includes applying one or more electrical pulses, and the duration of each pulse is about 90 to 110 microseconds.

79. The method of claim 65, wherein the step of applying an electric field includes applying a set of about 1 to 15 pulses.

80. The method of claim 79, wherein each pulse has a duration of about 90 to 110 microseconds.

81. The method of claim 65, wherein the step of applying an electric field includes applying a plurality of electrical pulses to produce a voltage gradient at the BPH tissue site in a range of from about 50 volt/cm to about 8000 volt/cm.

82. The method of claim 65, further comprising:
monitoring a temperature of the BPH tissue site; and
adjusting the electric field to maintain a temperature of 50 degrees C. or less at the BPH tissue site.

83. The method of claim 65, further comprising:
detecting a ratio of voltage across cells at the BPH tissue site to electric current through the cells; and
adjusting a magnitude of applied voltage to the BPH tissue site in accordance with changes in the ratio of voltage to current.

84. The method of claim 65, wherein the step of applying includes applying a plurality of electrical pulses through a switching device to activate treatment electrodes in a selected pattern.

* * * * *